United States Patent [19]

Humphreys et al.

[11] Patent Number: 4,532,111

[45] Date of Patent: Jul. 30, 1985

[54] RECOVERY OF CATALYSTS AS W, MO OR RU OXYCHLORIDES IN LIQUID PHASE CHLORINATION OF PYIRIDINE COMPOUNDS

[75] Inventors: Paula L. Humphreys, San Ramon; Jonathan A. Okorley, Antioch, both of Calif.

[73] Assignee: The Dow Chemical Company, Midland, Mich.

[21] Appl. No.: 632,182

[22] Filed: Jul. 19, 1984

[51] Int. Cl.$^3$ .................. C01G 55/00; C01G 41/00; C01G 39/00; C07D 213/26

[52] U.S. Cl. ........................................ 423/22; 423/55; 423/475; 502/23; 502/24; 546/345

[58] Field of Search ............... 502/23, 24, 32, 38, 502/30; 423/55, 475, 492, 22; 546/345

[56] References Cited

U.S. PATENT DOCUMENTS

| | | | |
|---|---|---|---|
| 1,911,505 | 3/1933 | Herold et al. | 423/492 |
| 4,227,001 | 10/1980 | Dietsche et al. | 546/345 |
| 4,256,894 | 3/1981 | Dietsche et al. | 546/345 |

Primary Examiner—P. E. Konopka

[57] ABSTRACT

Metal chloride catalysts employed in liquid phase chlorination reactions are recovered by treating the reaction mass with oxygen or air to form solid metal oxychloride compounds which can be separated and reused.

2 Claims, No Drawings

RECOVERY OF CATALYSTS AS W, MO OR RU OXYCHLORIDES IN LIQUID PHASE CHLORINATION OF PYIRIDINE COMPOUNDS

BACKGROUND OF THE INVENTION

Chlorinated pyridine derivatives are known compounds and have been prepared by a number of processes. Such processes include, for example, those described in U.S. Pat. Nos. 3,420,833; 3,244,722; 3,732,230; 3,186,994; 3,538,100; British Pat. No. 957,276 and copending application No. 16,646 filed Mar. 1, 1979. The products of these processes have been used as herbicides and pesticides and as chemical intermediates in the preparation of other highly desired herbicide or pesticide products. Of the many chlorinated pyridine derivatives, 2,3-dichloro-5-trichloromethylpyridine is a particularly desirable intermediate for the prepartion of selective herbicides having wide utility in the presence of valuable crops.

In copending application Ser. No. 467,710 filed Feb. 25, 1983, 2,3-dichloro-5-trichloromethylpyridine is prepared in high yields and high purity by a process which comprises contacting 2-chloro-5-trichloromethylpyridine in the liquid state with chlorine in the presence of a catalyst at a temperature of 70° to 250° C., the improvement comprising employing an effective amount of catalyst selected from the group consisting of tungsten hexachloride, molybdenum pentachloride, tungsten oxytetrachloride, molybdenum oxytetrachloride and ruthenium chloride. The preferred catalysts are those containing tungsten or molybdenum.

SUMMARY OF THE INVENTION

In accordance with this invention, the metal chloride catalysts employed in liquid phase chlorination reactions are recovered and recycled by treating the reaction mass with oxygen or air to form metal oxychloride compounds which are solids and can be recovered and recycled.

DETAILED DESCRIPTION OF THE INVENTION

The metal chloride catalysts employed in, for example, the liquid phase chlorination of 2-chloro-5-trichloromethylpyridine to prepare 2,3-dichloro-5-trichloromethylpyridine in high yields and purity are expensive and are oftentimes difficult to separate and recover from the reaction mass.

We have now found that by treating the said reaction mass with oxygen (air), preferably by passing air through said mass, the metal chloride catalysts employed in the reaction are converted to metal oxychlorides which are preferentially retained in the solids portion of the reaction mass, the desired organic product being recoverable from the liquid phase, and we have further found that said solids portion may be reused directly as a catalyst for further selective liquid phase chlorination. The treatment with air or oxygen may be carried out for several hours, advantageously for 8 to 20 hours or until the metal concentration in the supernatant liquid reaches the desired low level.

In a further embodiment we have found that said solids are more readily separable and reusable when the reaction mass is diluted with an inert solvent, e.g. methylene chloride, prior to treating with oxygen.

The air or oxygen treated catalyst may be employed over a temperature range of from about 70° to about 250° C. and is preferably employed at temperatures of from about 150° to 200° C.

The reactions are advantageously carried out under ambient pressure conditions, but higher or lower pressures may be employed if desired.

Reaction times vary with catalyst concentration as is known in the art.

The invention is further illustrated by the following Example.

EXAMPLE 1

Following the general procedure described in copending application Ser. No. 467,710 filed Feb. 25, 1983, 2-chloro-5-trichloromethylpyridine was chlorinated at 175° C. at ambient pressure in the presence of 0.5 mole percent fresh tungsten hexachloride. In 96 hours 77.4 weight percent of 2,3-dichloro-5trichloromethylpyridine was obtained.

Air was added to the final product mixture and the solid and liquid layers were separated by centrifuging. The liquid was found to contain 17 ppm tungsten. The solid (1.4 grams) was used to catalyze the chlorination of 187.6 grams of 2-chloro-5-trichloromethylpyridine at 200° C. and ambient pressure. In 98 hours, 77.5 weight percent of 2,3-dichloro-5-trichloromethylpyridine was obtained.

EXAMPLE 2

The reaction mass from a further run, originally containing 2 mole percent tungsten hexachloride (6.7 grams) was cooled and 100 ml methylene chloride were added. Air was bubbled through the mixture overnight and 6.7 grams of solid were easily collected. The supernatant liquid contained only 1 ppm tungsten. The solid was directly reusable as catalyst for further chlorination.

Various modifications may be made in the present invention without departing from the spirit or scope thereof and it is understood that we limit ourselves only as defined in the appended claims.

We claim:

1. A process for the recovery of tungsten, molybdenum or ruthenium chloride catalysts employed in the liquid phase chlorination of pyridine compounds which comprises treating the reaction mass with oxygen or air for a time sufficient to form solid tungsten, molybdenum or ruthenium oxychloride compounds and thereafter separating said solid compounds from the liquid phase.

2. Process of claim 1 wherein the metal chloride catalyst is tungsten hexachloride.

* * * * *